(12) United States Patent
Patel et al.

(10) Patent No.: US 10,383,811 B1
(45) Date of Patent: Aug. 20, 2019

(54) SUNSCREEN EMULSION COMPRISING SILANE-TREATED OXIDE

(71) Applicant: L'OREAL, Paris (FR)

(72) Inventors: Sonal Patel, Iselin, NJ (US); Balanda Atis, Newark, NJ (US)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 15/963,513

(22) Filed: Apr. 26, 2018

(51) Int. Cl.
| | |
|---|---|
| *A61K 8/27* | (2006.01) |
| *A61K 8/891* | (2006.01) |
| *A61K 8/81* | (2006.01) |
| *A61K 8/02* | (2006.01) |
| *A61K 8/06* | (2006.01) |
| *A61Q 17/04* | (2006.01) |
| *A61K 8/29* | (2006.01) |

(52) U.S. Cl.
CPC .............. *A61K 8/891* (2013.01); *A61K 8/025* (2013.01); *A61K 8/0279* (2013.01); *A61K 8/064* (2013.01); *A61K 8/066* (2013.01); *A61K 8/27* (2013.01); *A61K 8/29* (2013.01); *A61K 8/8141* (2013.01); *A61Q 17/04* (2013.01); *A61K 2800/30* (2013.01); *A61K 2800/612* (2013.01); *A61K 2800/651* (2013.01)

(58) Field of Classification Search
CPC ...... A61K 8/064; A61K 8/025; A61K 8/0279; A61K 8/27; A61K 8/29; A61K 2800/651; A61Q 17/04
See application file for complete search history.

(56) References Cited

U.S. PATENT DOCUMENTS

2008/0081024 A1* 4/2008 Beasley .................. A61K 8/37
424/59

OTHER PUBLICATIONS

"Protective Foundation SPF 33," MINTEL GNPD, record ID 4468891, published Dec. 2016, p. 1-2.
"Sheer Physical Protection SPF 50 PA ++++," MINTEL GNPD, record ID 3224043, published Aug. 2015, p. 1-2.
"Sheer Daily Protector SPF 50/PA ++++," MINTEL GNPD, record ID 3016535, published Mar. 2015, p. 1-2.
"CC Glow SPF 30 PA+++," MINTEL GNPD, record ID 2437611, published Aug. 2014, p. 1-2.
"CC Glow SPF 30 PA+++," MINTEL GNPD, record ID 2618635, published Aug. 2014, p. 1-2.
"BB Primer-Cream Daily Defense SPF 30," MINTEL GNPD, record ID 2483455, published Jun. 2014, p. 1-2.
"BB Primer-Cream Daily Defense SPF 30," MINTEL GNPD, record ID 2379931, published May 2014, p. 1-2.
"Styling Eyes," MINTEL GNPD, record ID 2320257, published Apr. 2014, p. 1-2.
"Luxury Compact Powder SPF 17," MINTEL GNPD, record ID 2318853, published Feb. 2014, p. 1-2.
"CC Glow Cream Broad Spectrum SPF 30," MINTEL GNPD, record ID 2156558, published Sep. 2013, p. 1-2.
"CC Mat Color & Shine Control," MINTEL GNPD, record ID 2060878, published Jun. 2013, p. 1-2.
"CC Mat Color & Shine Control," MINTEL GNPD, record ID 22202727, published Jun. 2013, p. 1-2.
"BB Matter with Signature Shinerase Broad Spectrum SPF 30," MINTEL GNPD, record ID 2031929, published May 2013, p. 1-2.
"Full Spectrum Brightening Makeup Base SPF 30/PA+++," MINTEL GNPD, record ID 1816057, published Jun. 2012, p. 1-2.
"Second Skin Liquid Foundation," MINTEL GNPD, record ID 1420081, published Oct. 2010, p. 1-2.
"Liquid Makeup," MINTEL GNPD, record ID 1189179, published Oct. 2009, p. 1-2.
"Teint Prodigieux Tinted Moisture Gel," MINTEL GNPD, record ID 306602, published Oct. 2004, p. 1-2.

* cited by examiner

*Primary Examiner* — Ernst V Arnold
(74) *Attorney, Agent, or Firm* — Michael Tyerech

(57) ABSTRACT

Compositions including an aqueous phase emulsified within an external fatty phase comprising at least one silicone are provided. The compositions include iron oxide having a silane-treated surface, zinc-oxide having a silane-treated surface, a titanium dioxide-silica composite particulate, and hollow spheres of acrylic polymer.

15 Claims, No Drawings

SUNSCREEN EMULSION COMPRISING SILANE-TREATED OXIDE

FIELD OF THE INVENTION

The present invention relates to cosmetic compositions and, in particular, sunscreen emulsions having silane-treated oxides.

DISCUSSION OF THE BACKGROUND

Cosmetic compositions with pigments in order to provide hiding power and color, such as those suitable for face make-up, are known. Cosmetic compositions including inorganic sunscreens including those without organic sunscreens are also known. However, the inventors have recognized that compositions with both pigments and inorganic sunscreens, particularly ones that deliver a high degree of protection from the sun (e.g., high SPF) are difficult to formulate. One problem with formulating such compositions is that incorporating relatively high levels of pigments and sunscreens is that the levels of pigments and sunscreens needed to provide various benefits to the user contribute to the composition's instability.

Accordingly, certain aspects of the present invention relate to compositions that are stable and have a pleasant aesthetic, can provide sun protection and can also provide color (tint) and/or hiding power.

SUMMARY OF THE INVENTION

According to one aspect of the invention, the present invention relates to compositions, that include an aqueous phase emulsified within an external fatty phase. The external fatty phase includes at least one silicone. The composition further includes an iron oxide particulate having a silane-treated surface; a zinc-oxide particulate having a silane-treated surface; a titanium dioxide particulate having a hydrophobic surface; a titanium dioxide-silica composite particulate; and hollow spheres of acrylic polymer.

According to another aspect of the invention, the present invention relates to methods of making up the skin. The method includes applying to said skin a composition that include an aqueous phase emulsified within an external fatty phase. The external fatty phase includes at least one silicone. The composition further includes an iron oxide particulate having a silane-treated surface; a zinc-oxide particulate having a silane-treated surface; a titanium dioxide particulate having a hydrophobic surface; a titanium dioxide-silica composite particulate; and hollow spheres of acrylic polymer.

It is to be understood that both the foregoing general description and the following detailed description are exemplary and explanatory only, and are not restrictive of the invention.

DETAILED DESCRIPTION OF THE INVENTION

As used herein, the expression "at least one" means one or more and thus includes individual components as well as mixtures/combinations.

Other than in the operating examples, or where otherwise indicated, all numbers expressing quantities of ingredients and/or reaction conditions are to be understood as being modified in all instances by the term "about," meaning within 10% to 15% of the indicated number.

"Actives basis" as used herein means considering only the particular component of ingredient (e.g., in a composition) and ignoring other chemically unrelated components that may be also be present in the same raw material source of that particular component.

"Film former" or "film forming agent" as used herein means any material such as, for example, a polymer or a resin that leaves a film on the substrate to which it is applied.

"Polymer" as used herein means a compound which is made up of at least two monomers.

"Keratinous materials" includes materials containing keratin such as hair, skin, eyebrows, lips and nails.

"Solids basis" as used herein means considering only components (e.g., in a composition) that are solid at room temperature and ignoring portions of the composition that are liquid, e.g., water and volatile solvents.

"Substituted" as used herein, means comprising at least one substituent. Non-limiting examples of substituents include atoms, such as oxygen atoms and nitrogen atoms, as well as functional groups, such as hydroxyl groups, ether groups, alkoxy groups, acyloxyalky groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, hydroxyalkyl groups, and polysiloxane groups. The substituent(s) may be further substituted.

"Volatile", as used herein, means having a flash point of less than about 100° C.

"Non-volatile", as used herein, means having a flash point of greater than about 100° C.

As used herein, all ranges provided are meant to include every specific range within, and combination of sub ranges between, the given ranges. Furthermore, notably the range description "from about 1%, 2% or 3% to about 5%, 10% or 15%," includes 1-5, 1-10, 1-15, 2-5, 2-10, 2-15, 3-5, 3-10, and 3-15.

All percentages of ingredients herein are listed on an actives basis unless specifically stated otherwise.

The term "substantially free" or "essentially free" as used herein means that there is less than about 2% by weight of a specific material added to a composition, based on the total weight of the compositions and may include less than about 1 wt. %, less than about 0.5 wt. %, less than about 0.1 wt. %, or none of the specified material.

The compositions of the present invention may be of various consistencies including, for example fluid, paste, semi-solid, and the like.

The composition of the invention includes an aqueous phase. The aqueous phase includes water and optionally other ingredients dissolved dispersed or suspended therein. The aqueous phase is emulsified within an external fatty phase. The external fatty phase includes at least one silicone and may also optionally include other ingredients dissolved dispersed or suspended therein.

Although the relative proportions of the aqueous phase and the fatty phase may vary, according to certain embodiments of the invention the fatty phase is present in a total concentration by weight that is greater than the aqueous phase emulsified therein. In certain embodiments of the invention there is sufficient aqueous phase present such that the concentration of water in the composition is from about 10% or 15% to about 30% or 40% by weight.

According to certain embodiments, the external fatty phase is characterized by a majority fraction of silicone fatty materials (also referred to herein as "silicones") and a minority fraction of non-silicone fatty materials. By "majority fraction of silicones," it is meant that greater than 50% by weight of the external fatty phase consists of one or more silicones. By "minority fraction of non-silicone fatty materials," it is meant that less than 50% by weight of the external fatty phase consists of one or more non-silicone fatty materials.

In certain notable embodiments, the composition is a water-in-oil (W/O) where the "O" represents a fatty phase comprising at least one silicone. In certain other embodiments, the composition is a double emulsion (W/O/W emulsion or O/W/O emulsion).

The compositions and methods of the present invention can comprise, consist of, or consist essentially of the essential elements and limitations of the invention described herein, as well as any additional or optional ingredients, components, or limitations described herein or otherwise useful in personal care.

Fatty Phase

The fatty phase includes one or more fatty materials, e.g., those compounds having a hydrophobic moiety and, in certain embodiments which are not amphiphilic and, as such, in this embodiment do not also include hydrophilic moieties, such as anionic, cationic, zwitterionic, or nonionic groups, that are polar, including sulfate, sulfonate, carboxylate, phosphate, phosphonate, ammonium, including mono-, di-, and trialkylammonium species, pyridinium, imidazolinium, amidinium, poly(ethyleneiminium), ammonioalkylsulfonate, ammonioalkylcarboxylate, amphoacetate, and poly(ethyleneoxy)sulfonyl moieties. In certain embodiments, the oil does not include hydroxyl moieties.

As described above, the fatty phase of compositions of the present invention include at least one silicone. By "silicone" or "silicone fatty material" it is meant a compound that includes two or more organosiloxane units, such as at least 5 of the organosiloxane units, in particular at least 10 organosiloxane units. In a notable embodiment, the at least one silicone is a silicone oil.

As used herein, by "silicone oil," it is meant compounds having a melting point of less than about 30C and generally insoluble in water and includes a two or more alkyl siloxy groups. Suitable examples of silicone oils include volatile silicone oils, such as those having a flash point from about 40° C. to about 100° C. be linear or cyclic, having a viscosity, at room temperature, of less than or equal to 6 cSt, and having from 2 to 7 silicon atoms, optionally substituted with alkyl or alkoxy groups of 1 to 10 carbon atoms. Examples of suitable volatile silicone oils include, octyltrimethicone, hexyltrimethicone, cyclopentasiloxane, cyclohexasiloxane, polydimethylsiloxanes. Other suitable examples of silicone oils include volatile silicone oils Non-volatile silicone oils include polymethylsiloxanes (PDMS) with a linear or cyclic silicone chain, which are liquid or pasty at room temperature, especially cyclopolydimethylsiloxanes (cyclomethicones) such as cyclohexasiloxane; polydimethyl-siloxanes (CTFA designation "dimethicones") comprising alkyl or alkoxy groups, which are pendent or at the end of a silicone chain, these groups containing from 2 to 24 carbon atoms; polydiethyl siloxanes; and dimethicone fluids having viscosity from about 300 cPs at 25° C. to about 1500 cPs at 25° C. Particularly useful dimethicone fluids have viscosity from about 350 cPs at 25° C. to about 1000 cPs at 25° C.

According to certain notable embodiments the at least one silicone in the fatty phase is or includes phenyl trimethicone.

Other silicones that may be included in the fatty phase include silicone resins such as those selected from the group consisting of siloxysilicate resins, silsesquioxane resins, and silicone elastomers such as dimethicone/vinyl dimethicone crosspolymers.

According to certain embodiments the concentration of the at least one silicone is from about 3%, 5% or 10% to about 20%, 30% or 40% by weight, including all ranges and sub-ranges therebetween.

Further, as described above, the fatty phase of the composition may further include one or more non-silicone fatty materials. Such non-silicone fatty materials are hydrophobic compounds that do not contain silicon.

The non-silicone fatty materials may have a carbon chain of at least six carbons in which none of the six carbons is a carbonyl carbon or has a hydrophilic moiety (defined below) bonded directly to it or have two or more oxypropylene groups in sequence. The hydrophobic moiety may include linear, cyclic, aromatic, saturated or unsaturated groups.

Suitable examples of such compounds of oils include vegetable oils (glyceryl esters of fatty acids, triglycerides) and fatty esters. Specific non-limiting examples include, without limitation, esters such as isopropyl palmitate, hexyl laurate, isohexadecane, isopropyl myristate, isononyl isononanoate C12-C15 alkyl benzoates, caprylic/capric triglycerides, pentaerythritol tetraoctanoate butyl octyl salicylate, and mineral oil.

According to certain other embodiments, the fatty phase may include one or more waxes. By wax, it is meant a lipophilic fatty compound that is solid at room temperature (about 25° C.) and atmospheric pressure (760 mm Hg, i.e., 105 Pa), which undergoes a reversible solid/liquid change of state and which has a melting point of greater than 30° C., and in some embodiments, greater than about 55° C. up to about 120° C. or even as high as about 200° C. The term wax may include waxes of animal origin, waxes of plant origin, waxes of mineral origin and waxes of synthetic origin. Examples of waxes of animal origin include beeswaxes, lanolin waxes and Chinese insect waxes. Examples of waxes of plant origin include rice waxes, carnauba wax, candelilla wax, ouricurry wax, cork fiber waxes, sugar cane waxes, Japan waxes, sumach wax and cotton wax. Examples of waxes of mineral origin include paraffins, microcrystalline waxes, montan waxes and ozokerites. Examples of waxes of synthetic origin include polyolefin waxes, e.g., polyethylene waxes, waxes obtained by Fischer-Tropsch synthesis, waxy copolymers and their esters, and silicone and fluoro waxes.

The term wax may further include high melting point hydrogenated oils of animal or plant origin. Examples include hydrogenated jojoba waxes and hydrogenated oils which are obtained by catalytic hydrogenation of fats composed of a $C_8$-$C_{32}$ linear or nonlinear fatty chain, hydrogenated sunflower oil, hydrogenated castor oil, hydrogenated copra oil, hydrogenated lanolin and hydrogenated palm oils.

Iron Oxide Particulate

Compositions of the present invention include an iron oxide particulate (a color pigment). The iron oxide particulate has a silane-treated surface. The iron oxide particulate provides hiding powder to aid in concealing skin imperfections while imparting some additional visible color. Any of various cosmetic grades of iron oxide particulate are suitable for use in compositions of the present invention. In certain embodiments the iron oxide particulate has an average particle size in a range from about 0.1 micron to about 10 microns, such as from about 0.15 micron to about 1 microns. Notable iron oxides include red, black and brown iron oxides having a primary particle size less than one micron and surface treated with an organosilane, such as triethoxycaprylyl silane. Suitable examples include SunPURO® Iran Oxides available from Sun Chemical of Parsippany, N.J.

The concentration of the iron oxide particulate in the composition may range from about 0.05%, 0.1%, 0.5% or 1.0% to about 2%, 6%, 10%, or 15% by weight, including all ranges and subranges therebetween. In certain notable embodiments, the concentration of the iron oxide particulate is at least about 1% by weight.

Zinc-Oxide Particulate

Compositions of the present invention include zinc oxide particulate having a silane-treated surface. The zinc oxide particulate provides a sunscreen effect (absorption/scattering of ultraviolet radiation from the sun to protect the users skin) and is an inorganic sunscreen.

Any of various cosmetic grades of zinc oxide particulate are suitable for use in compositions of the present invention. In certain embodiments the iron oxide particulate has an average particle size in a range from about 0.1 micron to about 10 microns, such as from about 0.15 micron to about 1 microns. One notable zinc oxide particulate suitable for use in the composition is Zano M Plus, a zinc oxide coated with triethoxycaprylylsilane, commercially available from EverZinc of Liege, Belgium.

The concentration of the zinc oxide particulate in the composition may range from about 0.1, 1%, or 7% to about 10% or 15% by weight. In certain notable embodiments, the inventors have found that high concentrations of zinc oxide particulate can be used and stabilized in the compositions. Accordingly, in certain embodiments, the concentration of the zinc oxide particulate in the composition is from about 5% to about 15% by weight, such as from about 7% to about 10% in the composition.

Titanium Dioxide Particulate

Compositions of the present invention include titanium oxide particulate having a hydrophobic-treated surface. The titanium dioxide particulate provides a sunscreen effect and is an inorganic sunscreen.

Any of various cosmetic grades of titanium oxide particulate having a hydrophobic-treated surface are suitable for use in compositions of the present invention. The hydrophobic treatment may be of various kinds known the art, including treatment with silanes, fatty acids or fatty esters and the like. In certain embodiments the titanium oxide particulate has an average particle size in a range from about 0.01 micron to about 100 microns, such as from about 1 micron to about 10 microns.

One notable titanium oxide particulate suitable for use in the composition is a titanium dioxide particulate having a primary particle size of about 15 nm and coated with aluminum hydroxide and stearic acid. An example is MICRO TITANIUM DIOXIDE MT-100 T V available from Tayca Corporation of Osaka, Japan.

Another notable titanium oxide particulate suitable for use in the composition is an oil dispersion of hydrophobically treated titanium dioxide particulate. An example is a dispersion of sterate-coated titanium dioxide in triethylhexanoin and isohexadecane using polyhydroxystearate dispersant, available as SOLAVEIL CT 200 from Croda Corporation of Edison, N.J.

Another notable titanium oxide particulate suitable for use in the composition is a titanium dioxide having a triethoxycaprylylsilane treated surface, available as RBTD-671-11S2 from Kobo Products, Inc. of South Plainfield, new Jersey.

The concentration of the titanium oxide particulate in the composition may range from about 1% to about 25% by weight. In certain notable embodiments, the inventors have found that high concentrations of titanium oxide particulate can be used and stabilized in the compositions. Accordingly, in certain embodiments, the concentration of the titanium oxide particulate in the composition is greater than about 10% by weight such as from about 13% to about 20% by weight in the composition.

According to certain embodiments, in order to enhance the stability of the particulates, the composition includes a dispersant.

Suitable dispersants include polyhydroxystearate, commercially available from, for example, Innospec Chemicals of Littleton, Colo. under the name DISPERSUN DSP-OL100 and DSP-OL300

Titanium-Dioxide-Silica Composite Particulate

Compositions of the present invention include a titanium dioxide-silica composite particulate. The titanium dioxide-silica composite particulate provides a sunscreen effect and is an inorganic sunscreen. While the titanium dioxide-silica composite particulate may have a hydrophobically-treated surface, in certain embodiments, it is free of such surface treatments. According to certain embodiments, titanium oxide-silica composite particulate is titanium dioxide coated with silica.

One notable titanium oxide-silica composite particulate suitable for use in the composition is a titanium dioxide coated with silica, An example is titanium dioxide encapsulated in a silica microsphere having an average particle size 5 microns, commercially available as Sunsil Tin50 from SUNJIN BEAUTY SCIENCE of Ansan, Gyeonggi, Korea.

Furthermore, according to certain embodiments of the invention, the iron oxide particulate having a silane-treated surface, the zinc-oxide particulate having a silane-treated surface, the titanium dioxide particulate having a hydrophobic surface, the titanium dioxide-silica composite particulate, and the hollow spheres of acrylic polymer are present in a combined concentration of less than about 40% by weight, such as from about 30% to about 40% by weight.

Emulsfiers

According to certain embodiments of the present invention, the composition may further optionally include emulsifiers and/or surfactants, primarily to assist in stabilizing oils in the composition and/or providing wetting or dispersing of the particulate portion. Any emulsifiers, surfactants, including anionic, nonionic, amphoteric, and cationic, emulsifiers or surfactants, may be used in the present invention, as long as the surfactant is cosmetically or dermatologically acceptable and suitable to stabilize an aqueous phase within an external fatty phase. In certain notable embodiments, the compositions include one or more non-ionic emulsifiers such as fatty acid esters of glycerol, ethoxylated fatty acids/esters, fatty alcohols and the like. The emulsifiers and surfactant may be used either singly or in combination two or more thereof. In one embodiment, the composition may include an alkoxylated non-ionic emulsifier. Particularly suitable emulsifiers include sorbitan isostearate and cetyl/PEG/PPG-20/1 dimethicone.

The concentration of emulsifiers and/or surfactants in the mascara may from about 0.5%, 1% or 2% by weight to about 5%, 8% or 15% by weight, including all combinations of such ranges, relative to the total weight of the composition.

Organic Sunscreens

Compositions of the present invention are, in certain embodiments, substantially free of organic sunscreens. By organic sunscreens it is meant organic compounds (e.g., those consisting substantially, predominantly or entirely of carbon, hydrogen, oxygen, and/or nitrogen atoms) that absorb ultraviolet radiation and are commonly used in cosmetic products in this regard. Non-limiting examples include p-aminobenzoic acid derivatives, anthranilates, benzophenones, camphor derivatives, cinnamic derivatives, dibenzoyl methanes, β,β-diphenylacrylate derivatives, salicylic derivatives, triazine derivatives, benzimidazole compounds, bis-benzoazolyl derivatives, methylene bis-(hydroxyphenylbenzotriazole) compounds, and the like.

Other Ingredients

Compositions of the present invention may optionally include other functional ingredients such as those that can be readily dissolved, dispersed or suspended in the composition. These may include other particulate materials (organic, silicone-based) or pigments; polymers such as for thickening/rheology modifying, film-forming, or water-resistance; preservatives; dyes, fragrances; antioxidants; vitamins; humectants, and the like. A person skilled in the art will take care to select the optional additional additives and/or the amount thereof such that the advantageous properties of the composition according to the invention are not, or are not substantially, adversely affected by the envisaged addition.

These substances may be selected variously by the person skilled in the art in order to prepare a composition which has the desired properties, for example, consistency or texture.

The other ingredients may be present in the composition in concentrations up to about 20%, such as from about 0%, 2%, or 5% to about 10%, 15%, or 20%, including all ranges and subranges therebetween.

According to preferred embodiments of the present invention, methods of protecting, caring for and/or making up a keratinous material by applying compositions of the present invention to the keratinous material in an amount sufficient to protect, care for and/or make up the keratinous material are provided. According to yet other preferred embodiments, methods of enhancing the appearance of a keratinous material by applying compositions of the present invention to the keratinous material in an amount sufficient to enhance the appearance of the keratinous material are provided.

In accordance with the preceding preferred embodiments, the compositions of the present invention are applied topically to the desired area of the keratinous material in an amount sufficient to protect, care for and/or make up the keratinous material, to cover or hide defects associated with keratinous material, or to enhance the appearance of keratinous material. The compositions may be applied to the desired area as needed, preferably once daily, and then preferably allowed to dry before subjecting to contact such as with clothing or other objects. Preferably, the composition is allowed to dry for about 4 minutes or less, more preferably for about 2 minutes or less.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective measurements.

The following examples are intended to illustrate the invention without limiting the scope as a result. The percentages are given on a weight basis.

Example A—Inventive Compositions

Compositions consistent with the ingredients and concentrations by weight in Table 1, below were prepared:

TABLE 1

| FUNCTION/TYPE | INVENTIVE EXAMPLE 1 | INVENTIVE EXAMPLE 2 |
|---|---|---|
| Silicones | 22% | 22% |
| Non-silicone fatty compounds | 11% | 11% |
| Silicone and non-silicone emulsifiers | 3% | 3% |
| Iron oxides | 10% | 6% |
| Hollow Spheres of Acrylic Polymer | 3% | 3% |
| Titanium dioxide particulates | 16% | 20% |
| Zinc oxide particulates | 8% | 8% |
| Titanium dioxide-silica composite particulate | 2% | 2% |
| Water | 20% | 20% |
| Other Ingredients | Q.S. | Q.S. |

Example B—Comparative Compositions

Compositions consistent with the ingredients and concentrations by weight in Table 2, below were prepared:

TABLE 2

| FUNCTION/TYPE | COMP. EX. 1 | COMP EX 2 | COMP EX 3 | COMP EX 4 |
|---|---|---|---|---|
| Silicones | 18% | 18% | 17% | 21% |
| Non-silicone fatty compounds | 14% | 14% | 10% | 12% |
| Silicone and non-silicone emulsifiers | 3% | 3% | 3% | 3% |
| Iron oxides | 10% | 10% | 10% | 10% |
| Hollow Spheres of Acrylic Polymer | 3% | 3% | 3% | 3% |
| Titanium dioxide particulates | 23% | 25% | 25% | 19% |
| Zinc oxide particulates | 7% | 7% | 7% | 8% |
| Titanium dioxide-silica composite particulate | 0% | 0% | 0% | 0% |
| Water | 22% | 18% | 17% | 21% |
| Other Ingredients | Q.S. | Q.S. | Q.S. | Q.S. |

The silicones, non-silicone fatty compounds, emulsifiers, hollow spheres of acrylic polymer, titanium dioxide particulate, and iron oxide particulate were combined together. These oils and powders were mixed using a Silverson mixer for 45 minutes under an ice bath to maintain temperature near ambient and while covered with aluminum foil. The zinc oxide was then added and the mixture was then ground for another 15 minutes. Samples were then evaluated visually between two glass slides to check for adequate dispersion. The mixture was then transferred to a Turotest/110V bench mixer, Type V2004 with chopper blade, available from VMI Mixing Company of Saint-Hilaire-de-Loulay, France, and the following additional ingredients were added: silicone elastomer, titanium dioxide-silica composite particulate, butylene glycol dicaprylate/dicaprate, and titanium dioxide coated with aluminum hydroxide and stearic acid and mixed for 30 minutes with the chopper blade to ensure uniformity. The side of the batch was scraped and the following water phase ingredients were added: water, magnesium sulfate, preservative, chelating agent, and butylene glycol fatty acid ester. After allowing to mix for 20 minutes, the emulsion was checked and them batched into jars.

The Inventive Examples shown in Table 1 and Comparative Examples shown in Table 2 were evaluated for stability after allowing to remain at room temp for about twenty-four hours. While the Inventive Examples showed no sign of phase instability, the Comparative Examples showed a clear visual phase instability (white layer on top) as the phases separated.

The foregoing description illustrates and describes the disclosure. Additionally, the disclosure shows and describes only the preferred embodiments but, as mentioned above, it is to be understood that it is capable to use in various other combinations, modifications, and environments and is capable of changes or modifications within the scope of the invention concepts as expressed herein, commensurate with the above teachings and/or the skill or knowledge of the relevant art. The embodiments described herein above are further intended to explain best modes known by applicant and to enable others skilled in the art to utilize the disclosure in such, or other, embodiments and with the various modifications required by the particular applications or uses thereof, accordingly, the description is not intended to limit the invention to the form disclosed herein. Also, it is intended to the appended claims to construed to include alternative embodiments.

What is claimed is:

1. A composition, comprising:
    an aqueous phase emulsified within an external fatty phase comprising at least one silicone;
    an iron oxide particulate having a silane-treated surface;
    a zinc-oxide particulate having a silane-treated surface;
    a titanium dioxide particulate having a hydrophobic surface;
    a titanium dioxide-silica composite particulate; and
    hollow spheres of acrylic polymer.

2. The composition of claim 1, wherein the concentration by weight of titanium dioxide particulate is greater than about 10%.

3. The composition of claim 1, wherein the concentration by weight of titanium dioxide particulate is from about 13% to about 20%.

4. The composition of claim 1, wherein the concentration by weight of zinc oxide particulate is from about 7% to about 10%.

5. The composition of claim 1, wherein the titanium dioxide-silica composite particulate is titanium dioxide coated with silica.

6. The composition of claim 1, further comprising a dispersant.

7. The composition of claim 1, further comprising polyhydroxystearate.

8. The composition of claim 1, wherein the concentration of water is from about 10% to about 40%.

9. The composition of claim 1, wherein the external fatty phase is characterized by a majority fraction of silicone fatty materials and a minority fraction of non-silicone fatty materials.

10. The composition of claim 1, wherein the concentration of the at least one silicone is from about 10% to about 40%.

11. The composition of claim 1, wherein the at least one silicone comprises phenyl trimethicone.

12. The composition of claim 1, wherein the iron oxide having a silane-treated surface is present in a concentration of at least about 1% by weight.

13. The composition of claim 1, wherein the composition is substantially free of organic sunscreens.

14. The composition of claim 1, wherein the iron oxide particulate having a silane-treated surface, the zinc-oxide particulate having a silane-treated surface, the titanium dioxide particulate having a hydrophobic surface, the titanium dioxide-silica composite particulate, and the hollow spheres of acrylic polymer are present in a combined concentration of less than about 40% by weight.

15. A method of making up the skin comprising applying the composition of claim 1 to said skin.

* * * * *